US008786862B2

(12) United States Patent
Wojtkowski et al.

(10) Patent No.: US 8,786,862 B2
(45) Date of Patent: Jul. 22, 2014

(54) SPECTRAL OPTICAL COHERENCE TOMOGRAPHY

(75) Inventors: Maciej Wojtkowski, Boniewo (PL); Maciej Szkulmowski, Torun (PL); Tomasz Bajraszewski, Torun (PL)

(73) Assignee: Optopol Technology SP. Z O.O, Zawiercie (PL)

( * ) Notice: Subject to any disclaimer, the term of this patent is extended or adjusted under 35 U.S.C. 154(b) by 247 days.

(21) Appl. No.: 13/003,453

(22) PCT Filed: Jul. 10, 2009

(86) PCT No.: PCT/EP2009/005020
§ 371 (c)(1),
(2), (4) Date: Jan. 10, 2011

(87) PCT Pub. No.: WO2010/003684
PCT Pub. Date: Jan. 14, 2010

(65) Prior Publication Data
US 2011/0122413 A1 May 26, 2011

(30) Foreign Application Priority Data

Jul. 11, 2008 (EP) .................................. 08012549

(51) Int. Cl.
*G01B 9/02* (2006.01)
*G01B 11/02* (2006.01)
*G02F 1/01* (2006.01)
*G02F 1/29* (2006.01)
*G02B 27/00* (2006.01)
*G01J 3/453* (2006.01)

(52) U.S. Cl.
CPC .......... *G01B 9/0201* (2013.01); *G01B 2290/35* (2013.01); *G01J 3/4535* (2013.01)
USPC ........... 356/479; 356/497; 356/455; 359/279; 359/298; 359/578

(58) Field of Classification Search
CPC . G01B 9/0201; G01B 2290/35; G01J 3/4535; G02F 1/01
USPC .......... 356/479, 497, 455, 452; 359/279, 298, 359/578
See application file for complete search history.

(56) References Cited

U.S. PATENT DOCUMENTS 5,301,010 A * 4/1994 Jones et al. .................... 356/479
6,061,136 A * 5/2000 Hayashi ........................ 356/495

(Continued)

FOREIGN PATENT DOCUMENTS

JP 200604733 2/2006
JP 2006078436 3/2006

(Continued)

OTHER PUBLICATIONS

Liu et al., "Rapid scanning all-reflective optical delay line of real-time optical coherence tomography," Optics Letters, 2004, 29(1):80-82.
Brezinski, "Optical Coherence Tomography: Principles and Applications," Section 6.4, pp. 151-156 (2006).
Huang et al., "Optical coherence tomography," Science, 254, pp. 1178-1181 (1991).

(Continued)

*Primary Examiner* — Gregory J Toatley
*Assistant Examiner* — Hina F Ayub
(74) *Attorney, Agent, or Firm* — Casimir Jones, S.C.

(57) ABSTRACT

The invention relates to an apparatus for generating a scannable optical delay for a beam of light and an apparatus for Fourier domain optical coherence tomography having said apparatus for generating a scannable optical delay in its reference arm (15). The light beam is directed to a pivotably driven mirror (10) from where it is reflected to a fixed mirror (12), and from there back retro reflected along the reference arm (5). Lens optics (9) are provided to ensure accurate optical alignment in several pivot positions of the pivotably driven mirror (10).

11 Claims, 2 Drawing Sheets

(56) References Cited

U.S. PATENT DOCUMENTS

| | | |
|---|---|---|
| 6,421,164 B2 | 7/2002 | Tearney et al. |
| 6,775,007 B2 * | 8/2004 | Izatt et al. ............... 356/497 |
| 7,180,600 B2 | 2/2007 | Horii et al. |
| 7,221,460 B2 * | 5/2007 | Ohtsuka ............... 356/508 |
| 7,349,098 B2 | 3/2008 | Li |
| 7,355,716 B2 | 4/2008 | De Boer et al. |
| 7,359,062 B2 | 4/2008 | Chen et al. |
| 2007/0019194 A1 * | 1/2007 | Chen et al. ............... 356/328 |

FOREIGN PATENT DOCUMENTS

| | | |
|---|---|---|
| WO | 2006/028210 | 3/2006 |
| WO | WO 2006/024152 | 3/2006 |

OTHER PUBLICATIONS

Huber et al., "Amplified, frequency swept lasers for frequency domain reflectometry and OCT imaging: design and scaling principles," Opt Express, 13, pp. 3513-3528 (2005).

Leitgeb et al., "Complex ambiguity-free Fourier domain optical coherence tomography through transverse scanning," Optics Letters, 32, pp. 3453-3455 (2007).

Liu et al., "Rapid scanning all-reflective optical delay line for real-time optical coherence tomography," Optics Letters, 29, pp. 80-82 (2004).

Szkulmowska et al., "Coherent noise-free ophthalmic imaging by spectral optical coherence tomography," J Physics D: Applied Physics, 38, pp. 2606-2611 (2005).

* cited by examiner

SPECTRAL OPTICAL COHERENCE TOMOGRAPHY

The present application is a §371 National Phase application of International Patent Application No. PCT/EP2009/005020, filed Jul. 10, 2009, incorporated herein by reference, which claims priority to European Patent Application Ser. No. 08 012 549.5, filed Jul. 11, 2008.

The invention relates to an apparatus for generating a scannable optical delay for a beam of light and to an apparatus for spectral optical coherence tomography.

Optical coherence tomography is a technique for examination of three-dimensional structures of partially transparent matter. According to this technique, partially coherent light is divided into two portions. One portion is used to illuminate the sample under investigation. The second portion is led through a reference path to be recombined with the light back-scattered from the sample. The recombined light contains an interferometric signal containing information about the internal structure of the sample. This information can be retrieved in essentially two different ways.

The first way, known as "Time domain Optical Coherence Tomography" (TdOCT), is based on a scannable optical path delay introduced in the reference path. The delay is scanned in an oscillating manner. In this case, interference fringes occur only in certain scan positions, namely in positions in which the optical path length of the reference path is identical with the optical path length for the light back-scattered by the sample. This enables determination of the relative distances of back-scattering structures within the sample (see Huang et al., Science, Vol. 254, 1991, p. 1178 to 1181).

The second way for retrieving information from the recombined light, known as "Fourier domain Optical Coherence Tomography" (FdOCT) is based on spectral analysis of the recombined light. The spectrum of the recombined light, i.e. the distribution of the light intensities for the various spectral components, is recorded. This can be performed by using either a spectrometer ("Spectral Optical Coherence Tomography", SOCT; see Szkulmowska et al., Journal of Physics D: Applied Physics, Vo. 38, 2005, 2606-2611), or a tuned light source ("Swept Source Optical Coherence Tomography", SS-OCT; see R. Huber et al., Optics Express, Vo. 13, 2005, 3513-3528).

While FdOCT, as opposed to TdOCT, by its nature does not require a scannable optical path delay (e.g. US 2005/0171438 A1), such delay may be desirable for certain modifications of FdOCT, e.g. for introduction of a phase shift (see US 2005/0018201 A1, par. [0042]). So there exists a permanent need for optimization of scannable optical path delays in respect of all optical coherence tomography variants.

According to US 2003/0025913 A1, there are various categories of scannable optical path delays which have been proposed for OCT. One category is based on group delay generation. It involves dispersive elements and thus severe adjustment problems, especially if the light beam in the reference path shall take essentially the same route when entering and exiting the reference path (e.g. US 2001/0036002 A1). Another category is based on variation of the path length with rotational methods, but still involves considerable adjustment problems. For instance, Liu et al., Optics Letters, Vol. 29, 2004, 80-82 proposed an improved scannable optical delay line comprising a pivotably driven mirror facing the incoming beam of light and reflecting it to a curved mirror from where the light is further reflected to a fixed flat mirror. While the performance of this arrangement is quite satisfactory in respect of scanning speed, it is difficult to adjust. In particular, angular alignment of the curved mirror is cumbersome. This is particularly disadvantageous in cases where it is desired that the entire scanning range be shifted to another scanning region.

The invention seeks to overcome these drawbacks and to satisfy the permanent need for simplification of adjustment of optical path delays. The solution is represented by the elements of claim 1. Claim 11 defines an apparatus for spectral optical coherence tomography in which the invention is employed in a mode in which the complex ambiguity artefact known in FdOCT (see Leitgeb et al., Optics Letters, Vol. 32, 2007, p. 3453-3455) is removed in an elegant manner. The further claims describe additional improvements of the invention.

The optical components used for the invention may be fiber or bulk optics or combinations thereof. Mirror optics and lens optics may each consist on a system of mirrors or lenses, respectively, and comprise suitable holding, adjusting and driving devices as far as required. The incoming beam is preferably collimated. Adjusting devices such as polarization controllers, dispersion compensators, mirrors or optical filters may be used where necessary.

A mirror may be any device eligible for reflecting at least a part of the incident light in a direction depending of the angle of the incoming light. For instance, a mirror may consist of the surface of a glass cube eligible for reflecting light. Preferred are however, conventional mirrors comprising a metallic layer and, optionally, further layers, e.g. from glass, for stabilization and protection. Flat mirrors are preferred over other mirror shapes. If the second mirror optics comprises a flat mirror, it is preferably aligned in such a way that the beam hits perpendicularly on this mirror.

A pivotably driven mirror may be a rotationally driven mirror. The driving mechanism may be of any kind. It may comprise a piezo transducer. Preferred are galvanometer drives due to their higher speed.

According to the invention, the beam is focused before it hits the pivotably driven scanning mirror and collimated thereafter so that a collimated beam hits second mirror in more than one, preferably a range of, pivot positions of the scanning mirror. This makes the system operable in several distances between the mirrors. Therefore, accurate alignment is simplified.

Advantageously, the first and second lens optics have the same focal lengths and are positioned in parallel. This further simplifies the alignment. Advantageously, the first and second lens optics consist of the same lens assembly. This simplifies the alignment even further. Further advantageously, lens assembly consists of a single lens. This keeps the set-up particularly simple. Arrangements employing the same lens assembly for both the first and second lens optics are further improved if the incoming light beam passes the first lens optics centrally. In these cases, alignment is particularly easy. On the other hand, if the apparatus is arranged in such a way that the incoming light beam passes the first lens optics eccentrically from the optical axis of the first lens optics, a larger scanning range is achieved as the range of angles for the reflection to the first lens optics is extended.

It is further advantageous if the first mirror optics is displaceable along the axis of the incoming light beam. Such a displacement causes a fourfold shift of the optical path length, whereas known set-ups, e.g. set-ups comprising corner-cubes, achieve twofold shifts only. It is further advantageous, in this case, if the focal lengths of the first and second lens optics are adjustable, preferably by shifting them together with the first mirror optics. This allows to readjustment if the shift causes the pivotably driven mirror to operate outside the focal planes of the lens optics. Preferably, and particularly if the first and second lens optics do not shift with the first mirror optics, the apparatus further comprises a focus controlling device arranged for automatically adjusting the focal lengths of the first and second lens optics to the distances between said first and second lens optics, respectively, and the first mirror optics. This disburdens the operator from readjusting manually.

Advantageously, the second mirror optics is displaceable in a direction parallel to the incident beam of light. This allows for a twofold shift of the optical path difference by shifting the second mirror optics only. A readjustment of the focal planes of any of the lens optics is not required in this case.

A further improvement is achieved if the second mirror optics comprises at least two mirrors in different optical distances to the first mirror optics. This arrangement allows for relatively large switches in the optical path lengths simply by pivoting the mirror of the first mirror optics so that the light beam is shifted between the mirrors of the second mirror optics. The optical path differences are preferably varied by varying the geometric distance rather than inserting media with varying refractive indexes to avoid dispersion and loss. These leaps in optical path differences may be utilized to expand the measuring range within the sample or to measure different ranges within the sample simultaneously or alternatingly.

According to a further improvement, the first lens optics focuses the beam of light on an area of the pivotably driven mirror displaced from the pivoting axis. This enables the invention to solve the problem of complex ambiguity artefacts as well. It is known in the art to introduce such a displacement for the beam hitting the scanning mirror and to use the phase shifts during the lateral scan (B-scan) to suppress the complex ambiguity artefacts with a Hilbert transform (Leitgeb et al., Optics Letters, Vol. 32, 2007, 3453-3455). The invention allows obtaining data eligible for suppression of complex ambiguity artefacts from the axial scan (A-scan) only. The invention relates, therefore, further to an apparatus for Fourier domain optical coherence tomography comprising a light source, an illumination path leading from the light source to a beam splitting device, a sample path leading from the splitting device to an area in which a sample under investigation may be placed, a reference path leading from said splitting device to a recombining device arranged for recombining the portion of light returning from the sample with the portion of light led through the reference path, and a detection path leading the recombined light to a detection device. This apparatus for Fourier domain optical coherence tomography according to the invention resolves the problem of complex ambiguity artefact removal with the help of an apparatus for generating a scannable optical delay for a beam of light according to the invention in which the first lens optics focuses the beam of light on an area of the pivotably driven mirror displaced from the pivoting axis.

Some embodiments of the invention as examples will now be described in greater detail with reference to drawings, in which.

Figure 1:
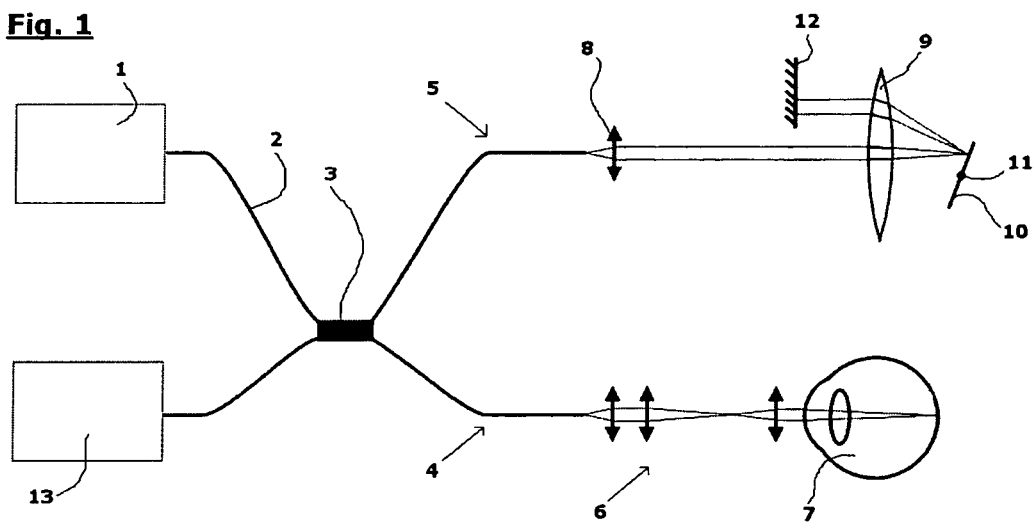
FIG. 1 is a schematic block diagram of an apparatus for optical coherence tomography according to the invention.

A light source 1, e.g. a superluminescent diode, emits light which is coupled into an optical fiber system 2. The light is directed to an optical coupler 3 acting as a splitting device of an interferometer. The light is thus split into one portion entering the sample path 4 and a second portion entering the reference path 5. A lens system 6 collimates the light portion in the sample path 4 and focuses this portion on the area under investigation within the sample 7. Surfaces within said sample 7 scatter portions of the incoming light back so that these portions return along the detection path 4 to the optical coupler 3. As shown in FIG. 1, the sample 7 is a human eye the lens of which is used to focus the light portion on a portion of the retina. In case of in vivo measurements with human or animal tissue, the result obtained from the use of the invention may help together with other facts known about the patient to make a diagnosis.

The light portion in the reference path 5 is collimated by a collimating lens 8 to impinge centrally and perpendicularly on a focusing lens 9 belonging to the apparatus for generating a scannable optical delay according to the invention. A mirror 10 which is rotatable about an axis 11 is placed in the focal plane of said focusing lens 9. It is positioned in such way that the point of impingement of the light portion coming from the focusing lens 9 is displaced from the axis of rotation 11. The rotatable mirror 10 reflects the light back to said focusing lens 9, but the point of impingement of the light on the focusing lens 9 is shifted in dependence of the angular position of the mirror 10.

Figure 2:
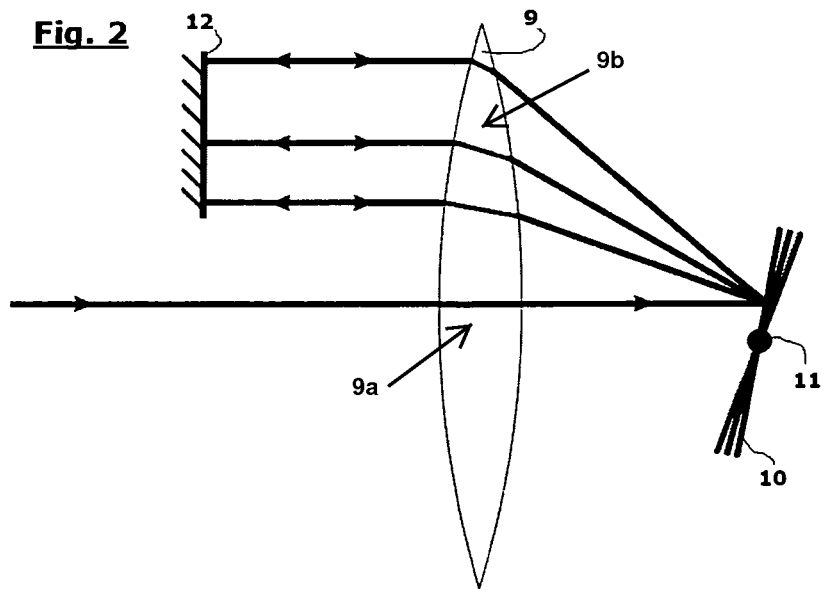
FIG. 2 is an enlarged view on the apparatus for generating an optical delay shown in FIG. 1.

As can be seen in greater detail in FIG. 2, the reflected beam of light is collimated by the focusing lens 9 in a range of pivot positions of the rotatable mirror 10. The rotatable mirror 10 is shown in three pivot positions in one instant for purposes of visualization only. In each of the pivot positions within the range, the beam is reflected by a fixed mirror 12 to propagate back along the reference path 5 to the optical coupler 3. The optical path difference in the reference path 5 changes with the variation of the pivot position of the rotatable mirror 10.

The optical coupler 3 acts as recombining device which superimposes the light portions returning from the sample path 4 and reference path 5. The recombined light beam contains an interference pattern, which depends essentially on the optical distances between the back-scattering surfaces within the sample 7 and the reference path 5 and the intensities of the light portions back-scattered by the surfaces within the sample 7.

The recombined light is guided from optical coupler 3 along a detection path to a detection device 13. The interference pattern contained in the light is recorded by detection device 13 and further processed as known by those skilled in the field of optical coherence tomography.

Figure 3:
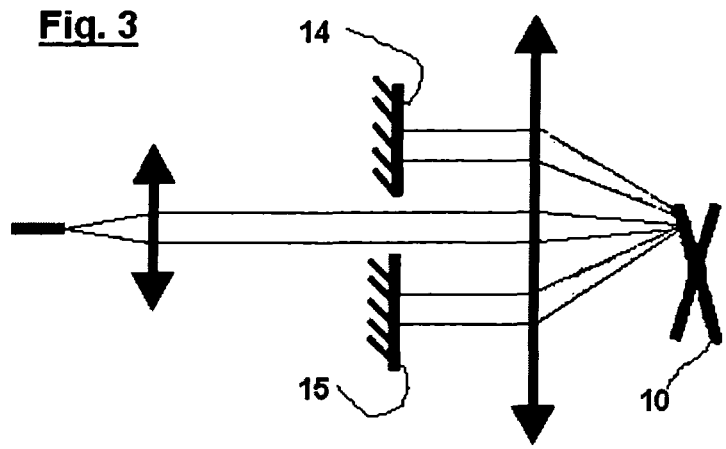
FIG. 3 shows an alternative embodiment of an apparatus for generating an optical delay according to the invention as a schematic block diagram.
Figure 4:
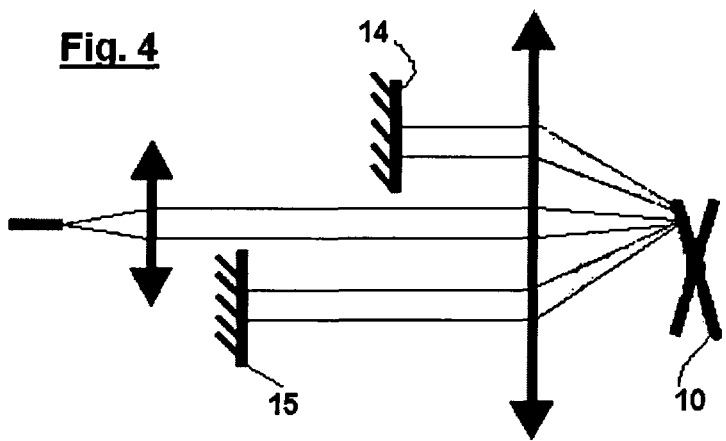
FIG. 4 illustrates a variation of the embodiment shown in FIG. 3.

In order to enlarge the scanning range of the apparatus for generating a scannable optical delay according to the invention, the second mirror optics may comprise mirrors placed on opposite sides of the incoming beam of light as shown in FIG. 3. For reasons of visualization, the angle between the pivot positions is largely exaggerated. The mirrors 14 and 15 of said second mirror optics may be areas of the surface of a single mirror with a hole, preferably a centric hole, through which the incoming beam of light passes. As shown in FIG. 4, the distance between mirror 14 and the rotatable mirror 10 is different from the distance between mirror 15 and said rotatable mirror 10. This allows for relatively large leaps of the optical path delay.

Figure 5:
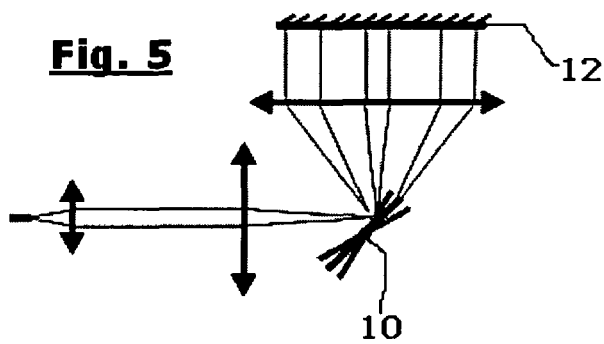
FIG. 5 shows another embodiment of the apparatus for generation an optical delay.

If the space requirements for the apparatus so require, the fixed mirror 12 may be placed elsewhere, e.g. so that its plane is parallel to the incoming light beam as shown in FIG. 5.

The invention claimed is:

1. Apparatus for generating a scannable optical delay for a beam of light comprising
   first mirror optics (10) providing a pivotably driven mirror facing the incoming beam of light and
   second mirror optics (12) arranged for reflecting the beam of light reflected by the first mirror optics (10) so that the beam of light hits the first mirror optics (10) again,
   first lens optics (9a) arranged for focusing the incoming beam of light on the pivotably driven mirror and
   second lens optics (9b) located between the first and second mirror optics and arranged for collimating the beam of light reflected by the mirror of said first mirror optics (10) in more than one pivot positions of said pivotably driven mirror,
   characterized in that
   the first lens optics (9a) and second lens optics (9b) have the same focal lengths and are positioned in parallel, and the optical elements of the apparatus are arranged such that
   i) the beam of light does not pass through or reflect off of a dispersive element of the apparatus on the path between said first mirror optics (10) and said second mirror optics (12), and
   ii) the optical delay changes with the variation of the pivot position of the rotatable mirror (10).

2. Apparatus according to claim 1, characterized in that first lens optics (9a) and second lens optics (9b) consist of the same lens assembly.

3. Apparatus according to claim 2, characterized in that the lens assembly consists of a single lens (9).

4. Apparatus according to claim 2, characterized in that the incoming light beam passes the first lens optics (9a) centrally.

5. Apparatus according to claim 2, characterized in that the incoming light beam passes the first lens optics (9a) eccentrically from the optical axis of the first lens optics.

6. Apparatus according to claim 1, characterized in that the first mirror optics (10) is displaceable along the axis of the incoming light beam.

7. Apparatus according to claim 6, characterized in that the focal lengths of the first lens optics (9a) and second lens optics (9b) are adjustable.

8. Apparatus according to claim 1, characterized in that the second mirror optics (12) is displaceable in a direction parallel to the incident beam of light.

9. Apparatus according to claim 1, characterized in that the second mirror optics (12) comprises at least two mirrors in different optical distances to the first mirror optics (10).

10. Apparatus according to claim 1, characterized in that said first lens optics (9a) focuses the beam of light on an area of the pivotably driven mirror displaced from the pivoting axis.

11. Apparatus for Fourier domain optical coherence tomography comprising
    a light source (1),
    an illumination path (2) leading from the light source (1) to a beam splitting device (3),
    a sample path (4) leading from the beam splitting device (3) to an area in which a sample (7) under investigation may be placed,
    a reference path (5) leading from said beam splitting device (3) to a recombining device (3) arranged for recombining the portion of light returning from the sample (7) with the portion of light led through the reference path (5), and a detection path leading the recombined light to a detection device (13),
    characterized in that
    an apparatus for generating a scannable optical delay for a beam of light according to claim 10 is provided in the reference path (5).

\* \* \* \* \*